(12) United States Patent
Hatzenbuhler et al.

(10) Patent No.: US 7,227,023 B2
(45) Date of Patent: Jun. 5, 2007

(54) QUINOLINE 3-AMINO CHROMAN DERIVATIVES

(75) Inventors: Nicole Theriault Hatzenbuhler, Bridgewater, NJ (US); Dahui Zhou, East Brunswick, NJ (US); Gary Paul Stack, Ambler, PA (US); Jonathan Laird Gross, Cranbury, NJ (US)

(73) Assignee: Wyeth, Madison, NJ (US)

( * ) Notice: Subject to any disclaimer, the term of this patent is extended or adjusted under 35 U.S.C. 154(b) by 161 days.

(21) Appl. No.: 10/835,128

(22) Filed: Apr. 29, 2004

(65) Prior Publication Data

US 2005/0004157 A1    Jan. 6, 2005

Related U.S. Application Data

(60) Provisional application No. 60/466,583, filed on Apr. 30, 2003.

(51) Int. Cl.
    *C07D 491/04*    (2006.01)
    *C07D 491/52*    (2006.01)
    *A61K 31/4741*    (2006.01)

(52) U.S. Cl. .......................... 546/80; 546/89; 514/291

(58) Field of Classification Search ................. 546/80, 546/89; 514/291
See application file for complete search history.

(56) References Cited

U.S. PATENT DOCUMENTS

| | | | | |
|---|---|---|---|---|
| 5,750,724 | A | 5/1998 | Kang et al. | 548/454 |
| 6,121,307 | A | 9/2000 | Mewshaw et al. | 514/414 |

FOREIGN PATENT DOCUMENTS

| | | |
|---|---|---|
| WO | 91/11435 A2 | 8/1991 |
| WO | 91/13872 A1 | 9/1991 |
| WO | 94/21608 A1 | 9/1994 |
| WO | WO 97/17343 AA1 | 5/1997 |
| WO | 02/066475 A2 | 8/2002 |
| WO | WO 03/010169 A1 | 2/2003 |
| WO | WO 2004/058746 A1 | 7/2004 |

OTHER PUBLICATIONS

Perez, V., et al., "Randomised double-blind, placebo-controlled trial of pindolol in combination with fluoxetine antidepressant treatment," *The Lancet*, 1997, 349: 1594-1597.

Feiger, A., "A Double-Blind Comparison of Gepirone Extended Release, Imipramine, and Placebo in the Treatment of Outpatient Major Depression," *Psychopharmacol. Bull.*, 1996, 32(4): 659-665.

Wilcox, C. et al., "A Double-Blind Trial of Low- and High-Dose Ranges of Gepirone-ER Compared With Placebo in the Treatment of Depressed Outpatients," *Psychopharmacol. Bull.*, 1996, 32(3): 335-342.

Grof, P. et al., "An open study of oral flesinoxan, a 5-$HT_{1A}$ receptor agonist, in treatment-resistant depression," *International Clinical Psychopharmacology*, 1993, 8: 167-172.

Dimitriou, E. et al., "Buspirone Augmentation of Antidepressant Therapy," *J. Clinical Psychopharmacol.*, 1998, 18(6): 465-469.

*Remingtons Pharmaceutical Sciences*, 17th edition, ed. Alfonoso R. Gennaro, Mack Publishing Company, Easton, PA (1985).

Bundgaard, (ed.), *Design of Prodrugs*, Elsevier (1985).

Higuchi and Stella (eds.) *Prodrugs as Novel Drug Delivery Systems*, American Chemical Society (1975).

Widder, et al. (ed.), *Methods in Enzymology*, vol. 4, Academic Press (1985).

Krogsgaard-Larsen, et al. (ed.), "Design and Application of Prodrugs", *Textbook of Drug Design and Development*, Chapter 5, 113-191 (1991).

Bundgaard, J. et al., "Glycolamide Esters as Biolabile Prodrugs of Carboxylic Acid Agents: Synthesis, Stability, Bioconversion, and Physicochemical Properties," *Pharmaceutical Sciences*, 77(4):285-298 (Apr. 1988).

Bundgaard, H. et al., "Prodrugs as a means to improve the delivery of peptide drugs," *Advanced Drug Delivery Reviews*, Elsevier Science Publishers, 8:1-38 (1992).

Cheetham, S. C. et al., "[$^3$H]Paroxetine Binding in Rat Frontal Cortex Strongly Correlates With [$^3$H]5-HT Uptake: Effect of Administration of Various Antidepressant Treatments," *Neuropharmacol.*, 1993, 32: 737-743.

Hall, M. D. et al. "[$^3$H]8-Hydroxy-2-(Di-n-Propylamino)Tetralin Binding to Pre- and Postsynaptic 5-Hydroxytryptamine Sites in Various Regions of the Rat Brain," *J. Neurochem.*, 1985, 44(6): 1685-1696.

Lazareno, S. and Birdsall, N.J.M., "Pharmacological characterization of acetylcholine-stimulated [$^{35}$S]-GTP$\gamma$S binding mediated by human muscarinic m1—m4 receptors: antagonist studies," *Br. J. Pharmacol.*, 1993, 109:1120-1127.

*Primary Examiner*—Rita Desai
(74) *Attorney, Agent, or Firm*—Woodcock Washburn LLP

(57) ABSTRACT

Quinoline 3-amino chroman derivatives and compositions containing such compounds are disclosed. Methods for using the quinoline 3-amino chroman derivatives and compositions containing such compounds in the treatment of serotonin disorders are disclosed. Also disclosed are processes for preparing quinoline 3-amino chroman derivatives.

8 Claims, No Drawings

QUINOLINE 3-AMINO CHROMAN DERIVATIVES

CROSS REFERENCE TO RELATED APPLICATIONS

The present application claims benefit of Provisional Application Ser. No. 60/466,583, filed Apr. 30, 2003, the disclosure of which is hereby incorporated by reference in its entirety.

FIELD OF THE INVENTION

The present invention relates to novel quinoline 3-amino chroman derivatives, processes for preparing such derivatives, and the use of such derivatives to treat a variety of psychological disorders. Preferred compounds of this invention display activity both as serotonin reuptake inhibitors and as 5-$HT_{1A}$ receptor agonists, and are useful in the treatment of serotonin-related disorders.

BACKGROUND OF THE INVENTION

Major depressive disorder affects an estimated 340 million people worldwide. Depression is the most frequently diagnosed psychiatric disorder and, according to the World Health Organization, is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also has been estimated to result in more than $40 billion in annual costs in the United States alone, due to premature death, lost productivity, and absenteeism.

Selective serotonin reuptake inhibitors (SSRIs) have had significant success in treating depression and related illnesses and have become among the most prescribed drugs since the 1980s. Some of the most widely known SSRIs are fluoxetine, sertraline, paroxetine, fluvoxamine and citalopram. Although they have a favorable side effect profile compared to tricyclic antidepressants (TCAs), they have their own particular set of side effects due to the nonselective stimulation of serotonergic sites. They typically have a slow onset of action, often taking several weeks to produce their full therapeutic effect. Furthermore, they have generally been found to be effective in less than two-thirds of patients.

SSRIs are believed to work by blocking the neuronal reuptake of serotonin, increasing the concentration of serotonin in the synaptic space, and thus increasing the activation of postsynaptic serotonin receptors. Although a single dose of a SSRI can inhibit the neuronal serotonin transporter, and thus would be expected to increase synaptic serotonin, clinical improvement has generally been observed only after long-term treatment. It has been suggested that the delay in onset of antidepressant action of the SSRIs is the result of an increase in serotonin levels in the vicinity of the serotonergic cell bodies. This excess serotonin is believed to activate somatodendritic autoreceptors, i.e., 5-$HT_{1A}$ receptors, reduce cell firing activity and, in turn, decrease serotonin release in major forebrain areas. This negative feedback limits the increment of synaptic serotonin that can be induced by antidepressants acutely. Over time, the somatodendritic autoreceptors become desensitized, allowing the full effect of the SSRIs to be expressed in the forebrain. This time period has been found to correspond to the latency for the onset of antidepressant activity [Perez, V., et al., *The Lancet*, 1997, 349: 1594–1597].

In contrast to the SSRIs, a 5-$HT_{1A}$ agonist or partial agonist acts directly on postsynaptic serotonin receptors to increase serotonergic neurotransmission during the latency period for the SSRI effect. Accordingly, the 5-$HT_{1A}$ partial agonists buspirone and gepirone [Feiger, A., *Psychopharmacol. Bull.*, 1996, 32(4): 659–665; Wilcox, C., *Psychopharmacol. Bull.*, 1996, 32(93): 335–342] and the 5-$HT_{1A}$ agonist flesinoxan [Grof, P., *International Clinical Psychopharmacology*, 1993, 8(3): 167–172] have shown efficacy in clinical trials for the treatment of depression. Furthermore, such agents are believed to stimulate the somatodendritic autoreceptors, thus hastening their desensitization and decreasing the SSRI latency period. An agent with a dual mechanism of antidepressant action would be expected to have greater efficacy and thus reduce the number of patients refractory to treatment. Indeed, buspirone augmentation to standard SSRI therapy has been shown to produce marked clinical improvement in patients initially unresponsive to standard antidepressant therapy [Dimitriou, E., *J. Clinical Psychopharmacol.*, 1998, 18(6): 465–469].

Lacking from the current therapy regime, however, is a single compound that effectively displays the dual mechanism of antidepressant action.

SUMMARY OF THE INVENTION

This invention provides novel quinoline 3-amino chroman derivatives. In preferred embodiments, the compounds of this invention inhibit serotonin reuptake and/or are agonists or partial agonists at the 5-$HT_{1A}$ receptor. Such preferred compounds are thus useful in the treatment of diseases affected by disorders of serotonin-affected neurological systems, such as depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, cocaine addiction, alcohol addiction, and sexual dysfunction.

In one aspect, the present invention provides, quinoline 3-amino chroman derivatives having formula I or II:

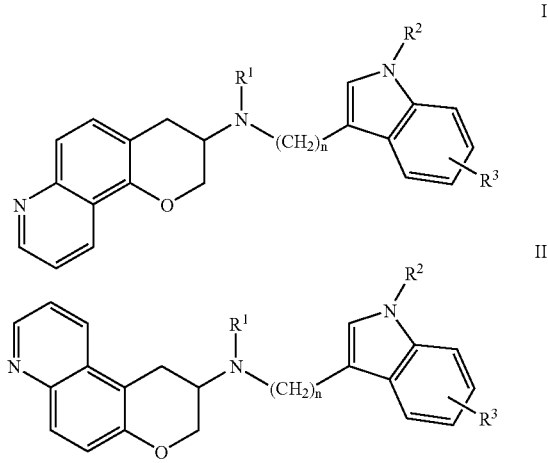

or a pharmaceutically acceptable salt thereof;
wherein $R^1$ is hydrogen, alkyl having 1 to 6 carbon atoms, cyclopropyl, cyclobutyl, cyclopentyl, cyclohexyl, methylcyclopropyl, or methylcyclobutyl;

$R^2$ is hydrogen or alkyl having 1 to 6 carbon atoms;

$R^3$ is hydrogen, fluoro, chloro, bromo, iodo, cyano at either the 5- or 6-position; and n is an integer from 2 to 4.

In another aspect, the present invention is directed to compositions comprising a compound of formula I or II and one or more pharmaceutically acceptable carriers.

Also provided methods for blocking the neuronal reuptake of serotonin and/or modulating the activity of $5\text{-HT}_{1A}$ receptors through in vitro or in vivo administration of an effective amount of one or more compound according to the invention. In this respect, such compounds preferably function as $5\text{-HT}_{1A}$ agonists.

The present invention also provides methods of treating a patient suspected of suffering from a serotonin-related disorder, comprising the step of administering to the patient a therapeutically effective amount of a compound of formula I or II.

In yet another aspect, the present invention is also directed to methods of inhibiting the uptake of serotonin in a patient in need thereof, comprising the step of administering to the patient a therapeutically effective amount of a compound of formula I or II.

DETAILED DESCRIPTION OF ILLUSTRATIVE EMBODIMENTS

The term "alkyl", as used herein, refers to an aliphatic hydrocarbon chain and includes, but is not limited to, straight and branched chains containing from 1–12 carbon atoms, preferably 1–6 carbon atoms. For example, methyl, ethyl, propyl, isopropyl, butyl, i-butyl and t-butyl are encompassed by the term alkyl.

This invention relates to both the R and S stereoisomers of the 3-amino-chroman, as well as to mixtures of the R and S stereoisomers. Throughout this application, the name of the product of this invention, where the absolute configuration of the 3-amino-chromans is not indicated, is intended to embrace the individual R and S enantiomers as well as mixtures thereof.

Where a stereoisomer is preferred, it may, in some embodiments, be provided substantially free of the corresponding enantiomer. Thus, "an enantiomer substantially free of the corresponding enantiomer" refers to a compound that is isolated or separated via separation techniques or prepared free of the corresponding enantiomer. "Substantially free", as used herein, refers to a compound made up of a significantly greater proportion of one stereoisomer. Stereoisomers may be isolated in pure form from racemic mixtures by standard separation techniques.

Preferred among the above noted $R^1$ groups are hydrogen and alkyl groups having 1 to 3 carbon atoms, with propyl being particularly preferred. Preferred $R^2$ groups are hydrogen and methyl, and preferred $R^3$ groups are hydrogen, fluoro, and cyano, with fluoro being particularly preferred at the 5-position of the indole. Preferred compounds are those of formula I or II in which $R^1$ is hydrogen or propyl, $R^2$ is hydrogen, $R^3$ is 5-fluoro, and n is an integer of 2, 3 or 4.

The following compounds are particularly preferred:

2,3-dihydro-1H-pyrano[3,2-f]quinolin-2-amine;

N-[3-(5-fluoro-1H-indol-3-yl)propyl]-2,3-dihydro-1H-pyrano[3,2-f]quinolin-2-amine;

N-[3-(5-fluoro-1H-indol-3-yl)propyl]-N-propyl-2,3-dihydro-1H-pyrano[3,2-f]quinolin-2-amine;

(+)-N-[3-(5-fluoro-1H-indol-3-yl)propyl]-2,3-dihydro-1H-pyrano[3,2-f]quinolin-2-amine;

(−)-N-[3-(5-fluoro-1H-indol-3-yl)propyl]-2,3-dihydro-1H-pyrano[3,2-f]quinolin-2-amine;

(−)-N-[3-(5-fluoro-1H-indol-3-yl)propyl]-N-propyl-2,3-dihydro-1H-pyrano[3,2-f]quinolin-2-amine;

(+)-N-[3-(5-fluoro-1H-indol-3-yl)propyl]-N-propyl-2,3-dihydro-1H-pyrano[3,2-f]quinolin-2-amine;

N-[2-(5-fluoro-1H-indol-3-yl)ethyl]-2,3-dihydro-1H-pyrano[3,2-f]quinolin-2-amine;

N-[2-(5-fluoro-1H-indol-3-yl)ethyl]-N-propyl-2,3-dihydro-1H-pyrano[3,2-f]quinolin-2-amine;

3,4-dihydro-2H-pyrano[2,3-f]quinolin-3-amine;

N-[3-(5-fluoro-1H-indol-3-yl)propyl]-3,4-dihydro-2H-pyrano[2,3-f]quinolin-3-amine;

N-[3-(5-fluoro-1H-indol-3-yl)propyl]-N-propyl-3,4-dihydro-2H-pyrano[2,3-f]quinolin-3-amine;

(+)-N-[3-(5-fluoro-1H-indol-3-yl)propyl]-3,4-dihydro-2H-pyrano [2,3-f]quinolin-3-amine;

(−)-N-[3-(5-fluoro-1H-indol-3-yl)propyl]-3,4-dihydro-2H-pyrano[2,3-f]quinolin-3-amine;

N-[4-(5-fluoro-1H-indol-3-yl)butyl]-3,4-dihydro-2H-pyrano[2,3-f]quinolin-3-amine; and N-[4-(5-fluoro-1H-indol-3-yl)butyl]-N-propyl-3,4-dihydro-2H-pyrano[2,3-f]quinolin-3-amine; and pharmaceutical salts thereof.

Scheme I: General Scheme to Produce Compounds of Formula I or II

The compounds of the invention are prepared by conventional methods. The appropriate 3-bromoalkyl indole 2 is combined with a quinoline 3-aminochroman derivative 1a or 1b in a solvent such as dimethyl sulfoxide in the presence of triethylamine and heated to a temperature of 80–100° C. for several hours as illustrated in Scheme I below. This is followed by reductive amination using sodium cyanoborohydride and the desired alkyl aldehyde to introduce the appropriate alkyl chain $R^1$ on the basic nitrogen if desired.

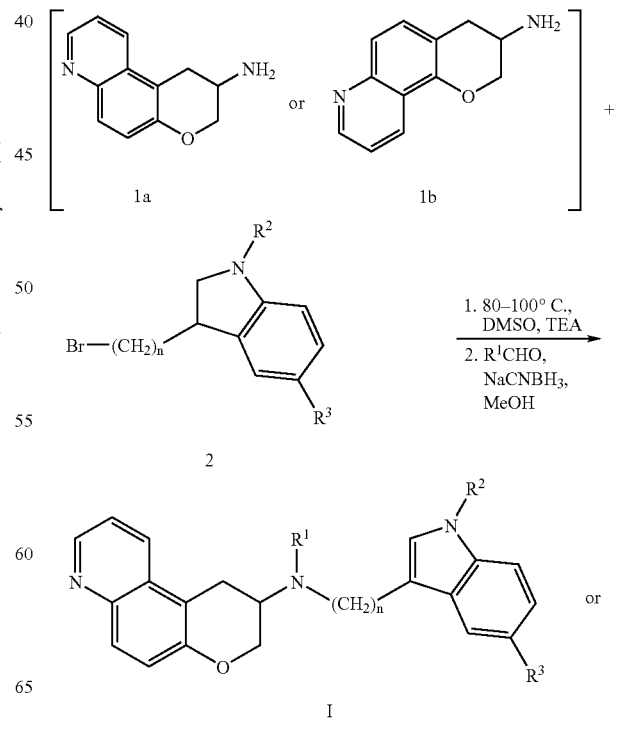

Scheme I

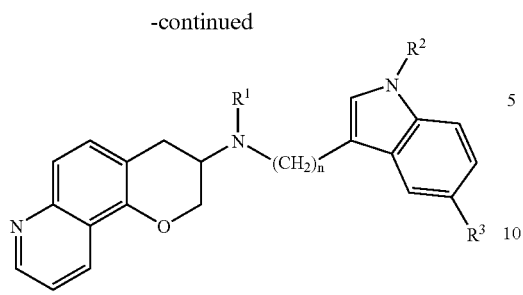

II

Alternatively, a 3-aminoalkyl indole can be used as starting material and combined with a quinoline chroman 3-carbonyl in the presence of a reducing agent such as sodium cyanoborohydride or sodium triacetoxyborohydride to generate the desired product of Formula I or II (where $R^1$ is H). This is followed by a second reductive amination using sodium cyanoborohydride and the desired alkyl aldehyde to introduce the appropriate alkyl chain $R^1$ on the basic nitrogen if desired. The compounds of the invention may be resolved into their enantiomers by conventional methods.

The 3-bromoalkyl indoles required to prepare the compounds of the invention are known compounds, and can be prepared by generally following the procedures taught by U.S. Pat. Nos. 5,750,724, 6,121,307 and 6,313,114. The 2,3-dihydro-1H-pyrano[3,2-f]quinolin-2-amine 1a and 3,4,-dihydro-2H-pyrano[2,3-f]quinolin-3-amine 1b are novel compounds, and can be prepared by the procedure illustrated below in Schemes II and III, respectively.

Scheme II: Preparation of 2,3-dihydro-1H-pyrano[3,2-f]quinolin-2-amine

The 2,3-dihydro-1H-pyrano[3,2-f]quinolin-2-amine 1a is prepared according to Scheme II. The commercially available 6-hydroxyquinoline 3 is first protected with an allyl group, and the resulting 6-allyloxyquinoline 4 subjected to Claisen rearrangement by heating in p-xylene to generate 5-allyl-quinolin-6-ol 5. The resulting phenol is protected with a suitable protecting group, such as benzyl, and the resulting product 6,5-allyl-6-benzyloxy-quinoline converted to the 3-(6-benzyloxy-quinoline-5-yl)-propane-1,2-diol 7 using the Sharpless Catalytic Asymmetric Dihydroxylation reagent, AD-mix-α. The diol is then converted to the bromoacetate 8 upon heating in 30% HBr in acetic acid, simultaneously cleaving the benzyl protecting group. Cyclization to 9 is achieved under basic conditions using sodium hydride. Cleavage of the acetyl group under basic conditions produced 10, 2,3-dihydro-1H-pyrano[3,2-f]quinolin-2-ol quantitatively. The tosylate 11 is then generated using p-toluenesulfonyl chloride in pyridine, and converted to the azide 12 with sodium azide in DMF. The azide is finally reduced by treatment with triphenylphosphine in THF-$H_2O$ to provide the 2,3-dihydro-1H-pyrano[3,2-f]quinolin-2-amine 1a suitable for the preparation of some of the derivatives claimed in this invention.

Scheme II

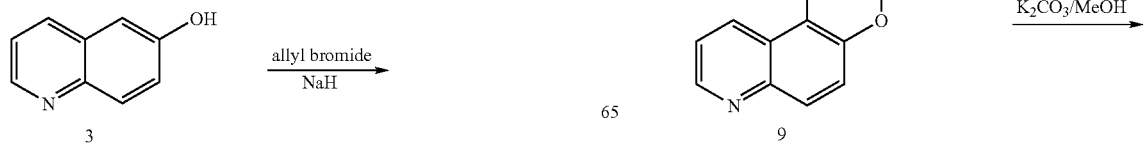

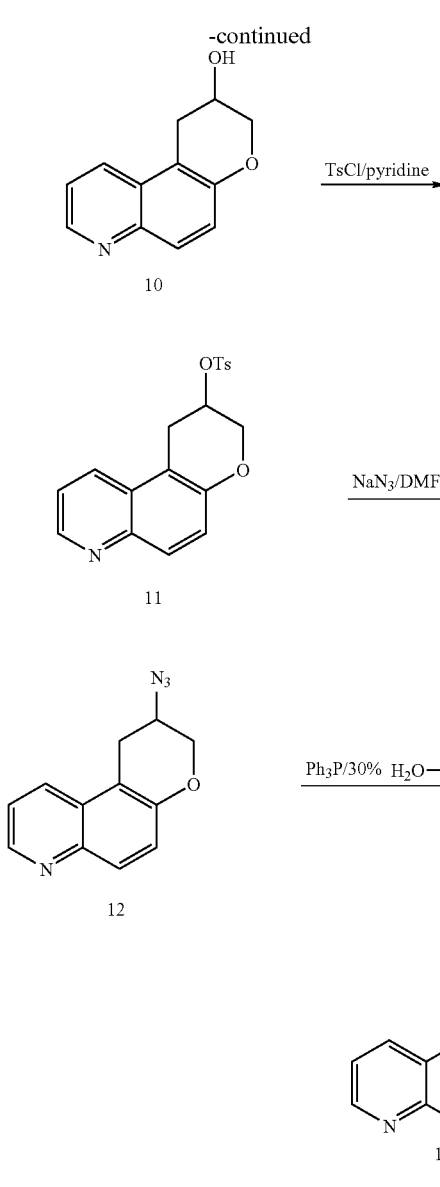

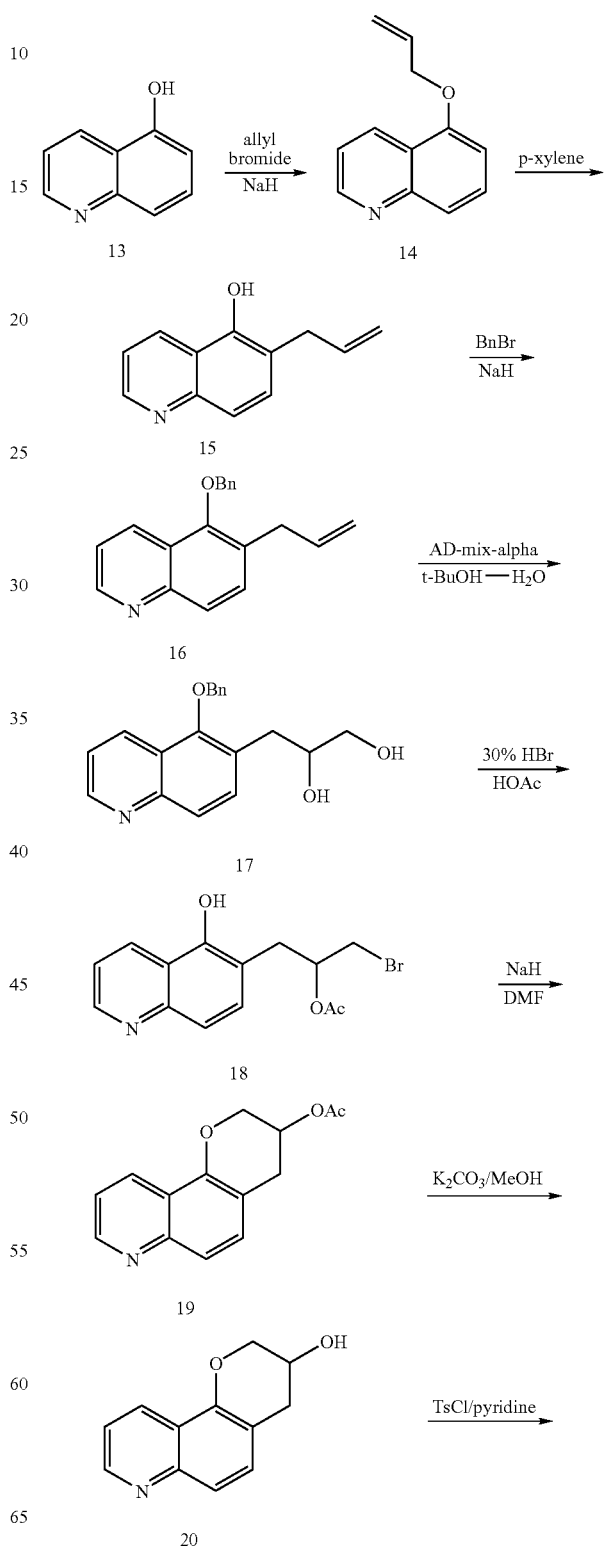

finally reduced by treatment with triphenylphosphine in THF-H$_2$O to provide the 3,4-dihydro-2H-pyrano[2,3-f] quinolin-3-amine 1b suitable for the preparation of some of the derivatives claimed in this invention.

Scheme III: Preparation of 3,4-dihydro-2H-pyrano[2,3-f] quinolin-3-amine

The 3,4-dihydro-2H-pyrano[2,3-f]quinolin-3-amine 1b is prepared according to Scheme III. The commercially available 5-hydroxyquinoline 13 is first protected with an allyl group, and the resulting 5-allyloxyquinoline 14 subjected to Claisen rearrangement by heating in p-xylene to generate 6-allyl-quinolin-5-ol 15. The resulting phenol is protected with a suitable protecting group, such as benzyl, and the resulting product 16, 6-allyl-5-benzyloxy-quinoline converted to the 3-(5-benzyloxy-quinoline-6-yl)-propane-1,2-diol 17 using the Sharpless Catalytic Asymmetric Dihydroxylation reagent, AD-mix-α. The diol is then converted to the bromoacetate 18 upon heating in 30% HBr in acetic acid, simultaneously cleaving the benzyl protecting group. Cyclization to 19 is achieved under basic conditions using sodium hydride. Cleavage of the acetyl group under basic conditions produced 20, 3,4-dihydro-2H-pyrano[2,3f]quinolin-3-ol quantitatively. The tosylate 21 is then generated using p-toluenesulfonyl chloride in pyridine, and converted to the azide 22 with sodium azide in DMF. The azide is

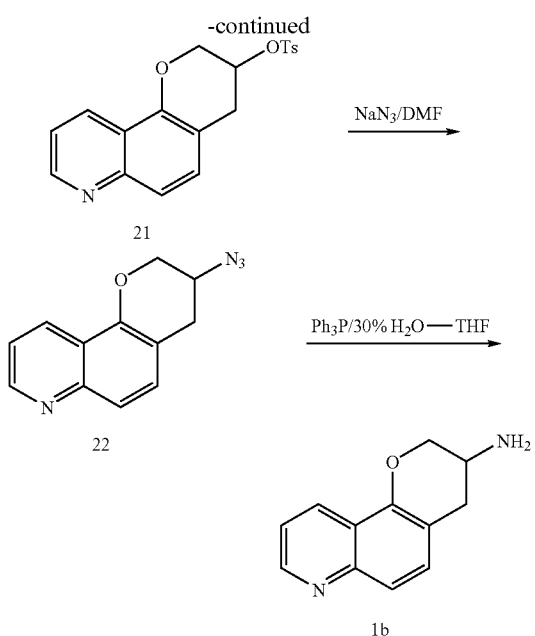

All enantiomers were separated by high performance liquid chromatography (HPLC) using a chiral column.

The terms "effective amount", "therapeutically effective amount" and "effective dosage" as used herein, refer to the amount of a compound of formula I or II that, when administered to a patient, is effective to at least partially ameliorate a condition form which the patient is suspected to suffer. Such conditions include, but are not limited to, depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, cocaine addiction, alcohol addiction, and sexual dysfunction.

The term "pharmaceutically acceptable salt", as used herein, refers to salts derived from organic and inorganic acids such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

The term "patient", as used herein, refers to a mammal, preferably a human.

The terms "administer", "administering" or "administration", as used herein, refer to either directly administering a compound or composition to a patient, or administering a prodrug derivative or analog of the compound to the patient, which will form an equivalent amount of the active compound or substance within the patient's body.

Compounds of formula I and II have been found to act as serotonin reuptake inhibitors and to have an affinity for the 5-HT$_{1A}$ reuptake transporter. They are therefore useful in the treatment of diseases affected by disorders of the serotonin affected neurological systems, including, but not limited to, depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, cocaine addiction, alcohol addiction, and sexual dysfunction. The present invention thus provides pharmaceutical compositions comprising at least either one compound of formula I or one compound of formula II, mixtures thereof, and optionally one or more pharmaceutically acceptable carriers, excipient, or diluents. The term "carrier", as used herein, shall encompass carriers, excipients, and diluents.

Examples of such carriers are well known to those skilled in the art and are prepared in accordance with acceptable pharmaceutical procedures, such as, for example, those described in *Remingtons Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of 0.01 to 100 mg/kg or preferably, at a dose range of 0.1 to 10 mg/kg. Such compositions may be administered from 1 to 6 times a day, more usually to 1 to 4 times a day.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient. Effective administration of the compounds of this invention may be given at an oral dose of from about 0.1 mg/day to about 1000 mg/day. Preferably, administration will be from about 10 mg/day to about 600 mg/day, more preferably, a starting dose is about 5 mg/day with gradual increase in the daily dose to about 150 mg/day, to provide the desired dosage level in the human. Doses may be administered in a single dose or in two or more divided doses. The projected daily dosages are expected to vary with route of administration.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, oculary (via eye drops), vaginally, and transdermally.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

The present invention includes prodrugs of compounds of either formula I or formula II. "Prodrug", as used herein means a compound which is convertible in vivo by metabolic means (e.g. by hydrolysis) to a compound of either formula I or formula II. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113–191 (1991), Bundgaard, et al., Journal of Drug Deliver reviews, 8:1–38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

The present invention further provides a compound of the invention for use as an active therapeutic substance. Compounds of the invention are of particular use in the treatment of diseases affected by disorders of serotonin.

The present invention further provides a method for treating depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, cocaine addiction, alcohol addiction, or sexual dysfunction in mammals including man, which comprises administering to the afflicted mammal an effective amount of a compound or a pharmaceutical composition of the invention.

EXAMPLES

The preparation of the intermediates utilized in Schemes II and III above and representative compounds of the invention is further illustrated below.

Example 1

Intermediate 4—6-allyloxyquinoline

To a suspension of sodium hydride (60%, 0.33 g, 8.3 mmol) in anhydrous N,N-dimethylformamide (30 ml) was added 6-hydroxyquinoline (1.0 g, 6.9 mmol) at room temperature. The reaction mixture was stirred for 1 hour, then allyl bromide (0.72 ml, 8.3 mmol) was added. The reaction mixture was allowed to stir for 1 hour at room temperature, quenched with water and extracted with methylene chloride. The organic layer was washed with water, dried over anhydrous sodium sulfate and filtered. The solvent was removed under vacuum. Chromatography (50% hexanes-ethyl acetate) afforded 1.14 g (89%) of 6-allyloxyquinoline as brown oil. MS ESI m/z 185 $[M+H]^+$.

Example 2

Intermediate 5—5-allyl-quinolin-6-ol

A solution of 6-allyloxyquinoline (intermediate 4) (1.14 g, 6.2 mmol) in p-xylene (30 ml) was allowed to reflux for 3 days. The organic solvent was removed under vacuum. Chromatography (30% hexanes-ethyl acetate) afforded 0.82 g (72%) of 5-allyl-quinolin-6-ol as a white solid: mp 162–164° C. Elemental Analysis for $C_{12}H_{11}NO$: Calculated: C, 77.81; H, 5.99; N, 7.56. Found: C, 77.82; H, 5.99; N, 7.45.

Example 3

Intermediate 6—5-allyl-6-benzyloxy-quinoline

To a suspension of sodium hydride (60%, 0.7 g, 16.8 mmol) in anhydrous N,N-dimethylformamide (80 ml) was added 5-allyl-quinolin-6-ol (intermediate 5) (2.68 g, 14 mmol) slowly at room temperature. The reaction mixture was stirred for 1 hour, then benzyl bromide (2.57 ml, 21 mmol) was added. The mixture was allowed to stir for 1.5 hrs at room temperature, quenched with water and extracted with methylene chloride. The organic layer was washed with water, dried over anhydrous sodium sulfate and filtered. The solvent was removed under vacuum. Chromatography (30% hexanes-ethyl acetate) afforded 3.6 g (92%) of 5-allyl-6-benzyloxy-quinoline as a light brown oil. MS ESI m/z 276 $[M+H]^+$.

Example 4

Intermediate 7—3-(6-benzyloxy-quinolin-5-yl)propane-1,2-diol

To a solution of commercially available AD-mix-α (20.2 g) in 2-methyl-2-propanol-water (30 ml: 40 ml) was added a solution of 5-allyl-6-benzyloxy-quinoline (intermediate 6) (4.28 g, 15.5 mmol) in 10 ml of 2-methyl-2-propanol slowly. The mixture was allowed to stir at room temperature for 18 hours, quenched with saturated sodium hydrogensulfide hydrate solution and extracted with methylene chloride. The organic layer was washed with water, dried over anhydrous sodium sulfate and filtered. The solvent was removed under vacuum. Chromatography (15% methanol-ethyl acetate) afforded 4.23 g (88%) of 3-(6-benzyloxy-quinolin-5-yl) propane-1,2-diol as an off-yellow solid: mp 160–162° C. Elemental Analysis for $C_{19}H_{19}NO_3$: Calculated: C, 73.77; H, 6.19; N, 4.53. Found: C, 73.39; H, 6.14; N, 4.41.

Example 5

Intermediate 8—acetic acid 1-bromomethyl-2-(6-hydroxyquinolin-5-yl)ethyl ester

A solution of 3-(6-benzyloxy-quinolin-5-yl)propane-1,2-diol (intermediate 7) (0.25 g) in 15 ml of hydrogen bromide (30 wt. % solution in acetic acid) was heated at 40° C. for 2 hrs. The reaction mixture was then poured into an ice bath, neutralized with 1N NaOH, and extracted with methylene chloride. The organic layer was washed with water, dried over anhydrous sodium sulfate and filtered. Chromatography (3% methanol-ethyl acetate) afforded 0.17 g (65%) of acetic acid 1-bromomethyl-2-(6-hydroxyquinolin-5-yl)ethyl ester as a white solid: mp 145.5–147.5° C. MS ESI m/z 324 $[M+H]^+$.

Example 6

Intermediate 9—2,3-dihydro-1H-pyrano[3,2-f]quinolin-2-yl acetate

To a suspension of sodium hydride (60%, 0.27 g, 6.6 mmol) in anhydrous N,N-dimethylformamide (30 ml) was added a pre-cooled solution of acetic acid 1-bromomethyl-2-(6-hydroxyquinolin-5-yl)ethyl ester (intermediate 8) (1.96 g, 6.0 mmol) in 10 ml of N,N-dimethylformamide at 0° C. The reaction mixture was stirred at 0° C. for 1 hr, quenched with water, and extracted with methylene chloride. The organic layer was washed with water, dried over anhydrous sodium sulfate and filtered. The solvent was removed under vacuum. Chromatography (10% hexanes-ethyl acetate) afforded 0.89 g (61%) of 2,3-dihydro-1H-pyrano[3,2-f]quinolin-2-yl acetate as a white solid: mp 125.4–127° C. MS ESI m/z 244 [M+H]$^+$. Elemental Analysis for $C_{14}H_{13}NO_3$: Calculated: C, 69.12; H, 5.39; N, 5.76. Found: C, 69.12; H, 5.48; N, 5.64.

Example 7

Intermediate 10—2,3-dihydro-1H-pyrano[3,2-f]quinolin-2-ol

To a solution of 2,3-dihydro-1H-pyrano[3,2-f]quinolin-2-yl acetate (intermediate 9) (0.49 g, 2 mmol) in methanol (20 ml) at 0° C. was added potassium carbonate (0.33 g, 2.4 mmol). The reaction mixture was stirred at 0° C. for 1 hr. The reaction mixture was poured into ice-$H_2O$ and extracted with methylene chloride. The organic layer was dried over anhydrous sodium sulfate, filtered and concentrated under vacuum to generate 0.37 g (91%) of 2,3-dihydro-1H-pyrano[3,2-f]quinolin-2-ol as a white solid: mp 160–161.5° C. MS ESI m/z 202 [M+H]$^+$.

Example 8

Intermediate 11—2,3-dihydro-1H-pyrano[3,2-f]quinolin-2-yl 4-methylbenzenesulfonate A solution of 2,3-dihydro-1H-pyrano[3,2-f]quinolin-2-ol (intermediate 10) (0.47 g, 2.3 mmol) and p-toluene sulfonyl chloride (0.89 g, 4.6 mmol) in anhydrous pyridine (20 mL) was stirred at room temperature for 2.5 days. It was then poured into ice-$H_2O$ and extracted with methylene chloride. The organic layer was dried over anhydrous sodium sulfate, filtered and concentrated under vacuum. Chromatography ((15:4:1) EtOAc-Hexane-MeOH) afforded 0.77 g (93%) of 2,3-dihydro-1H-pyrano[3,2-f]quinolin-2-yl 4-methylbenzenesulfonate as an off-white solid: mp 167.5–169.5° C. MS ESI m/z 356 [M+H]$^+$. Elemental Analysis for $C_{19}H_{17}NO_4S$: Calculated: C, 64.21; H, 4.82; N, 3.94. Found: C, 63.98; H, 4.79; N, 3.84.

Example 9

Intermediate 12—2,3-dihydro-1H-pyrano[3,2-f]quinolin-2-yl azide

A solution of 2,3-dihydro-1H-pyrano[3,2-f]quinolin-2-yl 4-methylbenzenesulfonate (intermediate 11) (0.58 g, 1.6 mmol) and sodium azide (1.6 g, 24 mmol) in anhydrous N,N-dimethylformamide (30 mL) was heated at 90° C. for 14 hrs. The reaction mixture was poured on ice-$H_2O$ and extracted with methylene chloride. The organic layer was washed with $H_2O$, dried over anhydrous sodium sulfate, filtered and concentrated under vacuum. Chromatography (10% MeOH/$CH_2Cl_2$) afforded 0.38 g (77%) of a mixture of 2,3-dihydro-1H-pyrano[3,2f]quinolin-2-yl azide and chromene by-product (20–25%). MS ESI m/z 227 [M+H]$^+$.

Example 10

Intermediate 1a—2,3-dihydro-1H-pyrano[3,2-f]quinolin-2-amine

A solution of 2,3-dihydro-1H-pyrano[3,2-f]quinolin-2-yl azide (intermediate 12) (2.05 g, 9.1 mmol) and triphenylphosphine (2.6 g, 9.9 mmol) in 30% water-tetrahydrofuran was allowed to reflux for 18 hrs. The solvent was removed under vacuum. Chromatography (10% methanol-methylene chloride) afforded 1.28 g (70%) of 2,3-dihydro-1H-pyrano[3,2f]quinolin-2-amine as an off-white solid. It was then converted to the HCl salt by dissolution in ethyl acetate and addition of 1M HCV/$Et_2O$ solution (2.4eq) to generate 2,3-dihydro-1H-pyrano[3,2f]quinolin-2-amine bishydrochloride salt an off-white solid: mp>180° C. MS ESI m/z 201 [M+H]$^+$. Elemental Analysis for $C_{12}H_{12}N_2O \cdot 2.00$ HCl·0.30 $H_2O$; Calculated: C, 51.74; H, 5.28; N, 10.06. Found: C, 51.94; H, 5.77; N, 9.49.

Example 11

Intermediate 14—5-allyloxyquinoline

This compound was prepared generally following the procedure above for intermediate 4, replacing 6-hydroxyquinoline with 5-hydroxyquinoline (10 g, 6.9 mmol). It was isolated in 85% yield (10.83 g) as a brown oil. MS ESI m/z 186 [M+H]$^+$.

Example 12

Intermediate 15—6-allyl-quinolin-5-ol

This compound was prepared generally following the procedure above for intermediate 5, replacing 6-allyloxyquinoline with 5-allyloxyquinoline (intermediate 14) (10.8 g, 58 mmol). It was isolated in 48% yield (5.18 g) as a white solid: mp 157–159° C. MS ESI m/z 186 [M+H]$^+$. Elemental Analysis for $C_{12}H_{11}NO$: Calculated: C, 77.81; H, 5.99; N, 7.56. Found: C, 77.60; H, 5.96; N, 7.41.

Example 13

Intermediate 16—6-allyl-5-benzyloxy-quinoline

This compound was prepared generally following the procedure above for intermediate 6, replacing 5-allyl-quinolin-6-ol with 6-allyl-quinolin-5-ol (intermediate 15) (5.17 g, 28 mmol). It was isolated in 100% yield (based on 2 gm of recovered starting material) as an off-white solid: mp 45–47° C. MS ESI m/z 276 [M+H]$^+$. Elemental Analysis for $C_{19}H_{17}NO$: Calculated: C, 82.88; H, 6.22; N, 5.09. Found: C, 82.80; H, 6.22; N, 5.06.

Example 14

Intermediate 17—3-(5-benzyloxy-quinolin-6-yl)-propane-1,2-diol

This compound was prepared generally following the procedure above for intermediate 7, replacing 5-allyl-6-benzyloxy-quinoline with 6-allyl-5-benzyloxy-quinoline (intermediate 16) (2.64 g, 9.6 mmol). It was isolated in 94% yield (9.0 g) as an off-white solid: mp 116–118° C. MS ESI m/z 310 [M+H]$^+$. Elemental Analysis for $C_{19}H_{19}NO_3$: Calculated: C, 73.77; H, 6.19; N, 4.53. Found: C, 73.82; H, 6.13; N, 4.57.

Example 15

Intermediate 18—acetic acid 1-bromomethyl-2-(5-hydroxyquinolin-6-yl)ethyl ester This compound was prepared generally following the procedure above for intermediate 8, replacing 3-(6-benzyloxy-quinolin-5-yl)propane-1,2-diol with 3-(5-benzyloxy-quinolin-6-yl)-propane-1,2-diol (intermediate 17) (0.43 g, 1.39 mmol). It was isolated in 66% yield (0.3 g) as a brown oil: MS ESI m/z 325 [M+H]$^+$.

Example 16

Intermediate 19—3,4-dihydro-2H-pyrano[2,3-f]quinolin-3-yl acetate

This compound was prepared generally following the procedure above for intermediate 9, replacing acetic acid 1-bromomethyl-2-(6-hydroxyquinolin-5-yl)ethyl ester with acetic acid 1-bromomethyl-2-(5-hydroxyquinolin-6-yl)ethyl ester (intermediate 18) (0.3 g, 0.92 mmol). It was isolated in 67% yield (0.15 g) as a clear oil: MS ESI m/z 244 [M+H]$^+$.

Example 17

Intermediate 20—3,4-dihydro-2H-pyrano[2,3-f]quinolin-3-ol

This compound was prepared generally following the procedure above for intermediate 10, replacing 2,3-dihydro-1H-pyrano[3,2-f]quinolin-2-yl acetate with 3,4-dihydro-2H-pyrano[2,3-f]quinolin-3-yl acetate (intermediate 19) (0.15 g, 0.62 mmol). It was isolated in 81% yield (0.10 g) as an off-white solid: mp 182–183.5° C. MS ESI m/z 202 [M+H]$^+$. Elemental Analysis for $C_{12}H_{11}NO_2$: Calculated: C, 71.63; H, 5.51; N, 6.96. Found: C, 71.50; H, 5.45; N, 6.83.

Example 18

Intermediate 21—3,4-dihydro-2H-pyrano[2,3-f]quinolin-3-yl 4-methylbenzenesulfonate This compound was prepared generally following the procedure above for intermediate 11, replacing 2,3-dihydro [3,2-f]quinolin-2-ol with 3,4-dihydro-2H-pyrano[2,3-f] quinolin-3-ol (intermediate 20) (1.37 g, 6.8 mmol). It was isolated in 59% yield (0.2 g) as a white solid: mp 119° C./dec. Elemental Analysis for $C_{19}H_{17}NO_4S$: Calculated: C, 64.21; H, 4.82; N, 3.94. Found: C, 63.96; H, 4.84; N, 3.83.

Example 19

Intermediate 22—3,4-dihydro-2H-pyrano[2,3-f]quinolin-3-yl azide

This compound was prepared generally following the procedure above for intermediate 12, replacing 2,3-dihydro-1H-pyrano[3,2-f]quinolin-2-yl 4-methylbenzenesulfonate with 3,4-dihydro-2H-pyrano[2,3-f]quinolin-3-yl 4-methylbenzenesulfonate (intermediate 21) (1.15 g, 3.2 mmol). It was isolated in 68% yield (0.5 g) as a light brown oil: MS ESI m/z 227 [M+H]$^+$.

Example 20

Intermediate 1b—3,4-dihydro-2H-pyrano[2,3-f] quinolin-3-amine

This compound was prepared generally following the procedure above for intermediate 1a, replacing 2,3-dihydro-1H-pyrano[3,2-f]quinolin-2-yl azide with 3,4-dihydro-2H-pyrano[2,3-f]quinolin-3-yl azide (intermediate 22) (0.5 g, 2.2 mmol). It was isolated in 68% yield (0.3 g) as a light pink solid: mp 247–248.5° C. MS ESI m/z 201 [M+H]$^+$. Elemental Analysis for $C_{12}H_{12}N_2O \cdot 0.1$ $H_2O$; Calculated: C, 71.34; H, 6.09; N, 13.87. Found: C, 71.23; H, 6.08; N, 13.70.

Example 21

N-[3-(5-fluoro-1H-indol-3-yl)propyl]-2,3-dihydro-1H-pyrano[3,2-f]quinolin-2-amine ("Compound 1")

A solution of 2,3-dihydro-1H-pyrano[3,2-f]quinolin-2-amine (intermediate 1a) (0.68 g, 3.4 mmol), 3-(3-bromopropyl)-5-fluoro-1H-indole (0.58 g, 2.26 mmol), and triethylamine (0.63 mL, 4.52 mmol) in anhydrous dimethylsulfoxide (40 mL) was stirred at 80° C. for 12 hrs. The reaction mixture was poured into ice-$H_2O$ and extracted with methylene chloride. The organic layer was dried over anhydrous sodium sulfate, filtered and concentrated under vacuum. Chromatography (5% MeOH/$CH_2Cl_2$) afforded 0.54 g (64%) of product as a brown oil. It was converted to the HCl salt by dissolution in ethyl acetate and addition of 1M HCl/$Et_2O$ solution (2.4 eq) to generate N-[3-(5-fluoro-1H-indol-3-yl)propyl]-2,3-dihydro-1H-pyrano[3,2-f]quinolin-2-amine bis-hydrochloride salt as a light brown solid: mp>180° C. MS ESI m/z 376 [M+H]$^+$. Elemental Analysis for $C_{23}H_{22}FN_3O \cdot 2.00$ $HCl \cdot 0.25$ $H_2O$; Calculated: C, 61.00; H, 5.45; N, 9.28. Found: C, 61.02; H, 5.66; N, 9.03.

Example 21a and 21b (+)-N-[3-(5-fluoro-1H-indol-3-yl)propyl]-2,3-dihydro-1H-pyrano[3,2-f]quinolin-2-amine and (−)-N-[3-(5-fluoro-1H-indol-3-yl)propyl]-2,3-dihydro-1H-pyrano[3,2-f]quinolin-2-amine ("Compounds 1a and 1b")

The enantiomers of N-[3-(5-fluoro-1H-indol-3-yl)propyl]-2,3-dihydro-1H-pyrano[3,2-f]quinolin-2-amine (example 21) were separated by chiral HPLC, isolated, and converted to the HCl salt as described above for the racemate, generating the following products:

(+)-N-[3-(5-fluoro-1H-indol-3-yl)propyl]-2,3-dihydro-1H-pyrano [3,2-f]quinolin-2-amine bis-hydrochloride salt (example 21a) as a yellow solid: mp 330° C./dec. $[\alpha]_D^{25}$=+36.5° (c=1% solution, DMSO). MS ESI m/z 376 [M+H]$^+$; Elemental Analysis for $C_{23}H_{22}FN_3O \cdot 2.00$ $HCl \cdot 0.50$ $H_2O$; Calculated: C, 60.40; H, 5.51; N, 9.19. Found: C, 60.66; H, 5.69; N, 9.12.

(−)-N-[3-(5-fluoro-1H-indol-3-yl)propyl]-2,3-dihydro-1H-pyrano[3,2-f]quinolin-2-amine bis-hydrochloride salt (example 21b) as a yellow solid: mp>460° C./dec. $[\alpha]_D^{25}$=−36.1° (c=1% solution, DMSO). MS ESI m/z 376

[M+H]+; Elemental Analysis for $C_{23}H_{22}FN_3O \cdot 2.00$ HCl·1.25 $H_2O$; Calculated: C, 58.67; H, 5.67; N, 8.92. Found: C, 58.85; H, 5.79; N, 8.67.

Example 22

N-[3-(5-fluoro-1H-indol-3-yl)propyl]-N-propyl-2,3-dihydro-1H-pyrano[3,2-f]quinolin-2-amine ("Compound 2")

To N-[3-(5-fluoro-1H-indol-3-yl)propyl]-2,3-dihydro-1H-pyrano[3,2-f]quinolin-2-amine (example 21) (0.13 g, 0.34 mmol) in anhydrous methanol (20 mL), was added propionaldehyde (0.25 mL, 3.4 mmol), acetic acid (0.2 ml, 0.34 mmol) and sodium cyanoborohydride (0.041 g, 0.65 mmol). The reaction mixture was stirred at room temperature overnight. The reaction mixture was quenched with 1N NaOH, and extracted with methylene chloride. The organic layer was dried over anhydrous sodium sulfate, filtered and concentrated under vacuum. Chromatography (5% MeOH/$CH_2Cl_2$) afforded 0.11 g (77%) of product as a clear oil. It was converted to the HCl salt by dissolution in ethyl acetate and addition of 1M HCl/$Et_2O$ (2.4 eq) to generate N-[3-(5-fluoro-1H-indol-3-yl)propyl]-N-propyl-2,3-dihydro-1H-pyrano[3,2-f]quinolin-2-amine bis-hydrochloride salt as a light yellow solid: mp>148° C. MS ESI m/z 416 [M–H]−. Elemental Analysis for $C_{26}H_{28}FN_3O \cdot 2.00$ HCl; Calculated: C, 63.67; H, 6.17; N, 8.57. Found: C, 63.97; H, 6.48; N, 8.28.

Example 23

(−)-N-[3-(5-fluoro-1H-indol-3-yl)propyl]-N-propyl-2,3-dihydro-1H-pyran[3,2-f]quinolin-2-amine ("Compound 3")

This compound was prepared generally following the procedure above for example 22 using (+)-N-[3-(5-fluoro-1H-indol-3-yl) propyl]-2,3-dihydro-1H-pyrano[3,2-f]quinolin-2-amine (example 21a) as starting material. It was converted to the HCl salt by dissolution in ethyl acetate and addition of 1M HCl/$Et_2O$ (2.4 eq) to generate (−)-N-[3-(5-fluoro-1H-indol-3-yl)propyl]-N-propyl-2,3-dihydro-1H-pyran[3,2-f]quinolin-2-amine bis-hydrochloride salt as a yellow solid: mp 83.5° C./dec. $[\alpha]_D^{25}$=−39.8° (c=1% solution, DMSO). MS ESI m/z 418 [M+H]+. Elemental Analysis for $C_{26}H_{28}FN_3O \cdot 2.00$ HCl·0.50 $H_2O$; Calculated: C, 62.53; H, 6.26; N, 8.41. Found: C, 62.69; H, 6.58; N, 8.20.

Example 24

(+)-N-[3-(5-fluoro-1H-indol-3-yl)propyl]-N-propyl-2,3-dihydro-1H-pyrano[3,2-f]quinolin-2-amine ("Compound 4")

This compound was prepared generally following the procedure above for example 22 using (−)-N-[3-(5-fluoro-1H-indol-3-yl)propyl]-2,3-dihydro-1H-pyrano[3,2-f]quinolin-2-amine (example 21b) as starting material. It was converted to the HCl salt by dissolution in ethyl acetate and addition of 1M HCl/$Et_2O$ (2.4 eq) to generate (+)-N-[3-(5-fluoro-1H-indol-3-yl)propyl]-N-propyl-2,3-dihydro-1H-pyrano[3,2-f]quinolin-2-amine bis-hydrochloride salt as a yellow solid: mp 106° C./dec. $[\alpha]_D^{25}$=+38.0° (c=1% solution, DMSO). MS ESI m/z 418 [M+H]+. Elemental Analysis for $C_{26}H_{28}FN_3O \cdot 2.00$ HCl; Calculated: C, 63.67; H, 6.17; N, 8.57. Found: C, 63.32; H, 6.39; N, 8.27.

Example 25

N-[2-(5-fluoro-1H-indol-3-yl)ethyl-2,3-dihydro-1H-pyrano[3,2-f]quinolin-2-amine ("Compound 5")

A solution of 2,3-dihydro-1H-pyrano[3,2-f]quinolin-2-amine (intermediate 1a) (0.42 g, 2.1 mmol), 3-(2-bromoethyl)-5-fluoro-1H-indole (0.39 g, 1.60 mmol), and triethylamine (0.22 mL, 3.20 mmol) in anhydrous dimethylsulfoxide (20 ml) was stirred at 100° C. for 9 hrs. The reaction mixture was poured into ice-$H_2O$ and extracted with methylene chloride. The organic layer was dried over anhydrous sodium sulfate, filtered and concentrated under vacuum. Chromatography (2% MeOH/$CH_2Cl_2$) afforded 0.22 g (38%) of product as a brown oil. It was converted to the HCl salt by dissolution in ethyl acetate and addition of 1M HCl/$Et_2O$ solution (2.4 eq) to generate N-[2-(5-fluoro-1H-indol-3-yl)ethyl-2,3-dihydro-1H-pyrano[3,2-f]quinolin-2-amine bis-hydrochloride salt as a green solid: mp 91° C./dec. MS ESI m/z 362 [M+H]+. Elemental analysis for $C_{22}H_{20}FN_3O \cdot 2.00$ HCl·1.50 $H_2O$; Calculated: C, 57.27; H, 5.46; N, 9.11. Found: C, 57.53; H, 5.29; N, 8.64.

Example 26

N-[2-(5-fluoro-1H-indol-3-yl)ethyl]-N-propyl-2,3-dihydro-1H-pyrano[3,2-f]quinolin-2-amine ("Compound 6")

This compound was prepared generally following the procedure above for example 22 using N-[2-(5-fluoro-1H-indol-3-yl)ethyl-2,3-dihydro-1H-pyrano[3,2-f]quinolin-2-amine (example 25) as starting material. It was converted to the HCl salt by dissolution in ethyl acetate and addition of 1M HCl/$Et_2O$ (2.4 eq) to generate N-[2-(5-fluoro-1H-indol-3-yl)ethyl]-N-propyl-2,3-dihydro-1H-pyrano[3,2-f]quinolin-2-amine bis-hydrochloride salt as a yellow solid: mp 67° C. MS ESI m/z 404 [M+H]+. Elemental Analysis for $C_{25}H_{26}FN_3O \cdot 2.00$ HCl·1.25 $H_2O$; Calculated: C, 60.18; H, 6.16; N, 8.42. Found: C, 60.49; H, 6.35; N, 8.16.

Example 27

N-[3-(5-fluoro-1H-indol-3-yl)propyl]-3,4-dihydro-2H-pyrano[2,3-f]quinolin-3-amine ("Compound 7")

This compound was prepared generally following the procedure above for example 21 using 3,4-dihydro-2H-pyrano[3,3-f]quinolin-3-amine (intermediate 1b) as starting material. It was converted to the HCl salt by dissolution in ethyl acetate and addition of 1M HCl/$Et_2O$ (2.4 eq) to generate N-[3-(5-fluoro-1H-indol-3-yl)propyl]-3,4-dihydro-2H-pyrano[2,3-f]quinolin-3-amine bis-hydrochloride salt as a yellow solid: mp 300° C./dec. MS (ESI) m/z 376 [M+H]+. Elemental analysis for $C_{23}H_{22}FN_3O \cdot 2.00$ HCl·0.25 $H_2O$; Calculated: C, 61.00; H, 5.45; N, 9.28. Found: C, 61.16; H, 5.72; N, 9.00.

Examples 27a and 27b (+)-N-[3-(5-fluoro-1H-indol-3-yl)propyl]-3,4,-dihydro-2H-pyrano[2,3-f]quinolin-3-amine and (−)-N-[3-(5-fluoro-1H-indol-3-yl)propyl]-3,4-dihydro-2H-pyrano[2,3-f]quinolin-3-amine ("Compounds 7a and 7b")

The enantiomers of N-[3-(5-fluoro-1H-indol-3-yl)propyl]-3,4-dihydro-2H-pyrano[2,3-f]quinolin-3-amine (example 27) were separated by chiral HPLC, isolated, and converted to the HCl salt as described above for the racemate, generating the following products:

(+)-N-[3-(5-fluoro-1H-indol-3-yl)propyl]-3,4-dihydro-2H-pyrano[2,3-f]quinolin-3-amine bis-hydrochloride salt (example 27a) as a light brown solid: mp 250° C./dec. $[\alpha]_D^{25}$=+27.14° (c=1% SOLUTION, DMSO). MS (ESI) m/z 376 [M+H]$^+$. Elemental Analysis for $C_{23}H_{22}FN_3O \cdot 2.00$ HCl·1.75 $H_2O \cdot 0.10$ $C_4H_8O_2$; Calculated: C, 57.51; H, 5.84; N, 8.60. Found: C, 57.41; H, 5.50; N, 8.58.

(−)-N-[3-(5-fluoro-1H-indol-3-yl)propyl]-3,4-dihydro-2H-pyrano[2,3-f]quinolin-3-amine bis-hydrochloride salt (example 27b) as a light brown solid: mp 250° C./dec. $[\alpha]_D^{25}$=−−17.99° (c=1% SOLUTION, DSMO). MS (ESI) m/z 376 [M+H]$^+$. Elemental Analysis for $C_{23}H_{22}FN_3O \cdot 2.00$ HCl·0.50 $H_2O \cdot 0.25$ $C_4H_8O_2O \cdot 0.20$ $C_4H_{10}O$; Calculated: C, 60.27; H, 5.91; N, 8.50. Found: C, 59.95; H, 6.15; N, 8.58.

Example 28

N-[3-(5-fluoro-1H-indol-3-yl)propyl]-N-propyl-3,4-dihydro-2H-pyrano[2,3-f]quinolin-3-amine ("Compound 8")

This compound was prepared generally following the procedure above for example 22 using N-[3-(5-fluoro-1H-indol-3-yl)propyl]-3,4-dihydro-2H-pyrano[2,3-f]quinolin-3-amine (example 27) as starting material. It was converted to the HCl salt by dissolution in ethyl acetate and addition of 1M HCl/Et$_2$O (2.4 eq) to generate N-[3-(5-fluoro-1H-indol-3-yl)propyl]-N-propyl-3,4-dihydro-2H-pyrano[2,3-f]quinolin-3-amine bis-hydrochloride salt as a yellow solid: mp 134° C./dec. MS (ESI) m/z 418 [M+H]$^+$. Elemental Analysis for $C_{26}H_{28}FN_3O \cdot 2.00$ HCl·0.75 $H_2O$; Calculated: C, 61.97; H, 6.30; N, 8.34. Found: C, 62.09; H, 6.60; N, 8.20.

Example 29

N-[4-(5-fluoro-1H-indol-3-yl)butyl]-3,4-dihydro-2H-pyrano[2,3-f]quinolin-3-amine ("Compound 9")

A solution of 3,4-dihydro-2H-pyrano[2,3-f]quinolin-3-amine (intermediate 1a) (0.20 g, 1.0 mmol), 3-(4-bromobutyl)-5-fluoro-1H-indole (0.19 g, 0.84 mmol), and triethylamine (0.28 mL, 1.68 mmol) in anhydrous dimethylsulfoxide (20 ml) was stirred at 100° C. for 14 hrs. The reaction mixture was poured into ice-H$_2$O and extracted with methylene chloride. The organic layer was dried over anhydrous sodium sulfate, filtered and concentrated under vacuum. Chromatography (5% MeOH/CH$_2$Cl$_2$) afforded 0.06 g (18%) of product as a light brown oil and unreacted starting material. It was converted to the HCl salt by dissolution in ethyl acetate and addition of 1M HCl/Et$_2$O solution (2.4 eq) to generate N-[4-(5-fluoro-1H-indol-3-yl)butyl]-3,4-dihydro-2H-pyrano[2,3-f]quinolin-3-amine bis-hydrochloride salt as an off-white solid: mp 173° C./dec. MS ESI m/z 390 [M+H]$^+$. Elemental Analysis for $C_{24}H_{24}FN_3O \cdot 2.00$ HCl·3.00 $H_2O$; Calculated: C, 55.82; H, 6.25; N, 8.14. Found: C, 55.57; H, 6.06; N, 7.76.

Example 30

N-[4-(5-fluoro-1H-indol-3-yl)butyl]-N-propyl-3,4-dihydro-2H-pyrano[2,3-f]quinolin-3-amine ("Compound 10")

This compound was prepared generally following the procedure above for example 22 using N-[4-(5-fluoro-1H-indol-3-yl)butyl]-3,4-dihydro-2H-pyrano[2,3-f]quinolin-3-amine (example 29) as starting material. It was converted to the HCl salt by dissolution in ethyl acetate and addition of 1M HCl/Et$_2$O solution (2.4 eq) to generate N-[4-(5-fluoro-1H-indol-3-yl)butyl]-N-propyl-3,4-dihydro-2H-pyrano[2,3-f]quinolin-3-amine bis-hydrochloride salt as a light brown solid: mp 164° C./dec. MS ESI m/z 432 [M+H]$^+$.

Example 31

Testing Affinity of Compounds for 5-HT Transporter

A protocol similar to that used by Cheetham et al. (*Neuropharmacol.*, 1993, 32: 737) was used to determine the affinity of the compounds of the invention for the serotonin transporter. The compound's ability to displace $^3$H-paroxetine from male rat cortical membranes was determined using a Tom Tech filtration device to separate bound from free $^3$H-paroxetine and Wallac 1205 Beta Plate® counter to quantitate bound radioactivity. $K_1$'s thus determined for standard clinical antidepressants are 1.96 nM for fluoxetine, 14.2 nM for imipramime and 67.6 nM for zimelidine. A strong correlation has been found between $^3$H-paroxetine binding in rat frontal cortex and $^3$H-serotonin uptake inhibition.

Example 32

Testing Affinity of Compounds for 5-HT$_{1A}$ Receptor

High affinity for the serotonin 5-HT$_{1A}$ receptor was established by testing the claimed compound's ability to displace [$^3$H] 8-OH-DPAT (dipropylaminotetralin) from the 5-HT$_{1A}$ serotonin receptor following a modification of the procedure of Hall et al. (*J. Neurochem.*, 1985, 44: 1685) which utilizes CHO cells stably transfected with human 5-HT$_{1A}$ receptors. The 5-HT$_{1A}$ affinities for the compounds of the invention are reported below as $K_1$s.

Example 33

Testing Agonist Activity of Compounds at the 5-HT$_{1A}$ Receptor

The agonist activity at 5-HT$_{1A}$ receptors was established by using a $^{35}$S-GTPγS binding assay similar to that used by Lazareno and Birdsall (*Br. J. Pharmacol.*, 1993, 109:1120). The binding assay determines the test compound's ability to affect the binding of $^{35}$S-GTPγS to membranes containing cloned human 5-HT$_{1A}$ receptors. Agonists produce an increase in binding whereas antagonists produce no increase but rather reverse the effects of the standard agonist 8-OH-DPAT. The test compound's maximum stimulatory effect is represented as the $E_{max}$, while its potency is defined by the $EC_{50}$.

The results of the three standard experimental test procedures described in the preceding three examples are reported below in Table 1.

TABLE 1

| Compound | 5-HT Transporter Affinity $K_I$ (nM) | 5-HT$_{1A}$ Receptor Affinity $K_I$ (nM) | 5-HT$_{1A}$ Function $EC_{50}$ (μM) ($E_{max}$) |
|---|---|---|---|
| 1 | 1.53 | 62.61 | 0.18 (75.82) |
| 2 | 6.50 | 91.03 | 2.22 (100) |

TABLE 1-continued

| Compound | 5-HT Transporter Affinity $K_I$ (nM) | 5-HT$_{1A}$ Receptor Affinity $K_I$ (nM) | 5-HT$_{1A}$ Function EC$_{50}$ (μM) (E$_{max}$) |
|---|---|---|---|
| 1a | 1.15 | 23.87 | 0.73 (100) |
| 1b | 2.50 | 313.80 | 0.12 (85.87) |
| 3 | 8.00 | 209.55 | 0.63 (54.72) |
| 4 | 19.00 | 239.20 | 0.30 (99.92) |
| 5 | 24.00 | Not tested | 5.00 (30) |
| 6 | 40.00 | 477.75 | 0.19 (41.27) |
| 7 | 2.83 | 13.63 | 1.20 (100) |
| 8 | 15.00 | Not tested | 1.71 (68.27) |
| 7a | 2.83 | Not tested | 0.32 (74.80) |
| 7b | 4.20 | 16.25 | 0.17 (100) |
| 9 | 1.18 | Not tested | 5.94 (100) |
| 10 | 12.00 | Not tested | Not tested |

Hence, the compounds of this invention are combined serotonin reuptake inhibitors/5-HT$_{1A}$ agonists, and are useful for the treatment of depression and other conditions related to or affected by the reuptake of serotonin and by the serotonin 1A receptor. Other conditions may be obsessive compulsive disorder, panic attacks, generalized anxiety disorder, sexual dysfunction, eating disorders, addictive disorders caused by ethanol or cocaine abuse and related illnesses.

When ranges are used herein for physical properties, such as molecular weight, or chemical properties, such as chemical formulae, all combinations and subcombinations or ranges and specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing form the spirit of the invention. It is, therefore, intended that the appended claims cover all such equivalent variations as fall within the true spirit and scope of the invention.

The invention claimed is:

1. A compound of formula I:

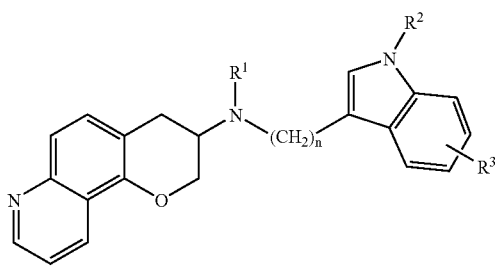

I or a pharmaceutically acceptable salt thereof;
wherein $R^1$ is hydrogen, alkyl having 1 to 6 carbon atoms, cyclopropyl, cyclobutyl, cyclopentyl, cyclohexyl, methylcyclopropyl, or methylcyclobutyl;
$R^2$ is hydrogen or alkyl having 1 to 6 carbon atoms;
$R^3$ is hydrogen, fluoro, chloro, bromo, iodo, cyano at either the 5- or 6- position; and
n is an integer from 2 to 4.

2. The compound of claim 1 wherein $R^1$ is propyl; $R^2$ is hydrogen; and $R^3$ is 5-fluoro.

3. The compound of claim 1 which is:
(rac)-3,4-dihydro-2H-pyrano[2,3-f]quinolin-3-amine;
(3R)-3,4-dihydro-2H-pyrano[2,3-f]quinolin-3-amine;
(3S)-3,4-dihydro-2H-pyrano[2,3-f]quinolin-3-amine;
(rac)-N-[3-(5-fluoro-1H-indol-3-yl)propyl]-3,4-dihydro-2H-pyrano[2,3-f]quinolin-3-amine;
(3R)-N-[3-(5-fluoro-1H-indol-3-yl)propyl]-3,4-dihydro-2H-pyrano[2,3-f]quinolin-3-amine;
(3S)-N-[3-(5-fluoro-1H-indol-3-yl)propyl]-3,4-dihydro-2H-pyrano[2,3-f]quinolin-3-amine;
(rac)-N-[3-(5-fluoro-1H-indol-3-yl)propyl]-N-propyl-3,4-dihydro-2H-pyrano[2,3-f]quinolin-3-amine;
(3R)-N-[3-(5-fluoro-1H-indol-3-yl)propyl]-N-propyl-3,4-dihydro-2H-pyrano[2,3-f]quinolin-3-amine;
(3S)-N-[3-(5-fluoro-1H-indol-3-yl)propyl]-N-propyl-3,4-dihydro-2H-pyrano[2,3-f]quinolin-3-amine;
(rac)-N-[4-(5-fluoro-1H-indol-3-yl)butyl]-3,4-dihydro-2H-pyrano[2,3-f]quinolin-3-amine;
(3R)-N-[4-(5-fluoro-1H-indol-3-yl)butyl]-3,4-dihydro-2H-pyrano[2,3-f]quinolin-3-amine;
(3S)-N-[4-(5-fluoro-1H-indol-3-yl)butyl]-3,4-dihydro-2H-pyrano[2,3-f]quinolin-3-amine;
(rac)-N-[4-(5-fluoro-1H-indol-3-yl)butyl]-N-propyl-3,4-dihydro-2H-pyrano[2,3-f]quinolin-3-amine;
(3R)-N-[4-(5-fluoro-1H-indol-3-yl)butyl]-N-propyl-3,4-dihydro-2H-pyrano[2,3-f]quinolin-3-amine; or
(3S)-N-[4-(5-fluoro-1H-indol-3-yl)butyl]-N-propyl-3,4-dihydro-2H-pyrano[2,3-f]quinolin-3-amine.

4. A composition comprising the compound of claim 1 and one or more pharmaceutically-acceptable carriers.

5. A compound of formula II

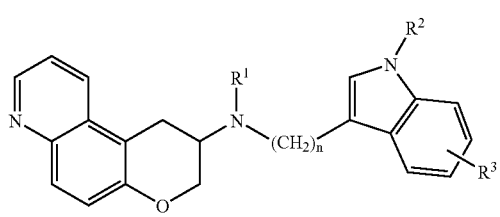

II or a pharmaceutically acceptable salt thereof;
wherein $R^1$ is hydrogen, alkyl having 1 to 6 carbon atoms, cyclopropyl, cyclobutyl, cyclopentyl, cyclohexyl, methylcyclopropyl, or methylcyclobutyl;
$R^2$ is hydrogen or alkyl having 1 to 6 carbon atoms;
$R^3$ is hydrogen, fluoro, chloro, bromo, iodo, cyano at either the 5- or 6-position; and
n is an integer from 2 to 4.

6. The compound of claim 5 wherein $R^1$ is propyl; $R^2$ is hydrogen; and $R^3$ is 5-fluoro.

7. The compound of claim 5 which is:
(rac)-2,3-dihydro-1H-pyrano[3,2-f]quinolin-2-amine;
(2R)-2,3-dihydro-1H-pyrano[3,2-f]quinolin-2-amine;
(2S)-2,3-dihydro-1H-pyrano[3,2-f]quinolin-2-amine;
(rac)-N-[3-(5-fluoro-1H-indol-3-yl)propyl]-2,3-dihydro-1H-pyrano[3,2-f]quinolin-2-amine;
(2R)-N-[3-(5-fluoro-1H-indol-3-yl)propyl]-2,3-dihydro-1H-pyrano[3,2-f]quinolin-2-amine;
(2S)-N-[3-(5-fluoro-1H-indol-3-yl)propyl]-2,3-dihydro-1H-pyrano[3,2-f]quinolin-2-amine;
(rac)-N-[3-(5-fluoro-1H-indol-3-yl)propyl]-N-propyl-2,3-dihydro-1H-pyrano[3,2-f]quinolin-2-amine;

(2R)-N-[3-(5-fluoro-1H-indol-3-yl)propyl]-N-propyl-2,3-dihydro-1H-pyrano[3,2-f]quinolin-2-amine;

(2S)-N-[3-(5-fluoro-1H-indol-3-yl)propyl]-N-propyl-2,3-dihydro-1H-pyrano[3,2-f]quinolin-2-amine;

(rac)-N-[2-(5-fluoro-1H-indol-3-yl)ethyl]-2,3-dihydro-1H-pyrano[3,2-f]quinolin-2-amine;

(2R)-N-[2-(5-fluoro-1H-indol-3-yl)ethyl]-2,3-dihydro-1H-pyrano[3,2-f]quinolin-2-amine;

(2S)-N-[2-(5-fluoro-1H-indol-3-yl)ethyl]-2,3-dihydro-1H-pyrano[3,2-f]quinolin-2-amine;

(rac)-N-[2-(5-fluoro-1H-indol-3-yl)ethyl]-N-propyl-2,3-dihydro-1H-pyrano[3,2-f]quinolin-2-amine;

(2R)-N-[2-(5-fluoro-1H-indol-3-yl)ethyl]-N-propyl-2,3-dihydro-1H-pyrano[3,2-f]quinolin-2-amine; or (2S)-N-[2-(5-fluoro-1H-indol-3-yl)ethyl]-N-propyl-2,3-dihydro-1H-pyrano[3,2-f]quinolin-2-amine.

8. A composition comprising the compound of claim 5 and one or more pharmaceutically-acceptable carriers.

\* \* \* \* \*